(12) United States Patent
Chee

(10) Patent No.: US 7,144,699 B2
(45) Date of Patent: Dec. 5, 2006

(54) ITERATIVE RESEQUENCING

(75) Inventor: Mark Chee, Del Mar, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/381,480

(22) PCT Filed: Mar. 19, 1998

(86) PCT No.: PCT/US98/05451

§ 371 (c)(1),
(2), (4) Date: Dec. 10, 1999

(87) PCT Pub. No.: WO98/41657

PCT Pub. Date: Sep. 24, 1998

(65) Prior Publication Data

US 2002/0025520 A1 Feb. 28, 2002

Related U.S. Application Data

(60) Provisional application No. 60/041,435, filed on Mar. 20, 1997, and provisional application No. 60/073,853, filed on Feb. 2, 1998.

(51) Int. Cl.
*C12Q 1/68* (2006.01)
*C12M 1/36* (2006.01)
*C07H 21/04* (2006.01)

(52) U.S. Cl. .................. 435/6; 435/283.1; 435/287.2; 536/23.1; 536/24.31

(58) Field of Classification Search .............. 435/6, 435/7.1, 91.1, 91.2; 436/518, 501; 536/23.1, 536/23.5, 24.32, 24.3, 25.3; 935/6, 77, 78; 422/50, 68.1
See application file for complete search history.

(56) References Cited

U.S. PATENT DOCUMENTS

| | | | |
|---|---|---|---|
| 5,202,231 A | 4/1993 | Drmanac et al. ............ 435/6 |
| 5,310,893 A * | 5/1994 | Erlich et al. ............ 536/24.31 |
| 5,436,327 A | 7/1995 | Southern et al. ......... 536/25.34 |
| 5,492,806 A | 2/1996 | Drmanac et al. ............ 435/5 |
| 5,525,464 A | 6/1996 | Drmanac et al. ............ 435/6 |
| 5,667,667 A | 9/1997 | Southern .................. 205/687 |
| 5,667,972 A | 9/1997 | Drmanac et al. ............ 435/6 |
| 5,683,881 A | 11/1997 | Skiena ..................... 435/6 |
| 5,695,940 A | 12/1997 | Drmanac et al. ............ 435/6 |
| 5,698,391 A * | 12/1997 | Cook et al. .................. 435/5 |
| 5,700,637 A | 12/1997 | Southern .................... 435/6 |
| 5,795,714 A * | 8/1998 | Cantor et al. |
| 5,861,243 A * | 1/1999 | Dietrich et al. ............... 435/5 |
| 5,972,619 A | 10/1999 | Drmanac et al. ............. 435/6 |
| 6,018,041 A | 1/2000 | Drmanac et al. .......... 536/24.3 |
| 6,025,136 A | 2/2000 | Drmanac et al. ............. 435/6 |
| 6,027,880 A * | 2/2000 | Cronin et al. ................. 435/6 |
| 6,045,997 A * | 4/2000 | Futreal et al. |
| 6,054,270 A | 4/2000 | Southern .................... 435/6 |
| 6,228,575 B1 * | 5/2001 | Gingeras et al. ............. 435/5 |

FOREIGN PATENT DOCUMENTS

| | | |
|---|---|---|
| EP | 386 229 | 4/1990 |
| EP | 373 203 | 6/1990 |
| EP | 392 546 | 10/1990 |
| EP | 514 927 A1 | 11/1992 |
| WO | WO 89/10977 | 11/1989 |
| WO | WO 90/03382 | 4/1990 |
| WO | WO 93/22480 | 11/1993 |
| WO | WO 95/11995 A1 | 5/1995 |
| WO | WO 98/31836 | 7/1998 |
| WO | WO 98/41657 | 9/1998 |
| WO | WO 99/39004 | 8/1999 |

OTHER PUBLICATIONS

Horwitz et al., "Novel Human Endogenous Sequences Related to Human Immunodeficiency Virus Type 1", *Journal of Virology*, vol. 66, No. 4, pp. 2170–2179, Apr. 1992.*
Hacia et al., "Evolutionary sequence comparisons using high–density oligonucleotide arrays," *Nature Genetics*, 18:155–158 (1998).
Kozal et al "Extensive polymorphisms observedin HIV–1 clade B protease gene using high–density oligonucleotide arrays" Nature Medicine, Jul. 7 19996; 753–759.*

* cited by examiner

*Primary Examiner*—B J Forman
(74) *Attorney, Agent, or Firm*—Townsend and Townsend and Crew, LLP

(57) ABSTRACT

The invention provides iterative methods of analyzing a target nucleic acid that represents a variant of a reference nucleic acid. An array of probes is designed to be complementary to an estimated sequence of a target nucleic acid. The array of probes is then hybridized to the target nucleic acid. The target sequence is reestimated from hybridization pattern of the array to the target nucleic acid. A further array of probes is then designed to be complementary to the reestimated sequence, and this array is used to obtain a further reestimate of the sequence of the target nucleic acid. By performing iterative cycles of array design and target sequence estimation, the estimated sequence of the target converges with the true sequence.

15 Claims, No Drawings

ITERATIVE RESEQUENCING

CROSS-REFERENCE TO RELATED APPLICATIONS

This application derives priority from 60/041,435 filed Mar. 20, 1997, 60/073,853 filed Feb. 2, 1998 and Townsend and Townsend and Crew filed Feb. 2, 1998, each of which is incorporated by reference in its entirety for all purposes.

TECHNICAL FIELD

The invention resides in the technical fields of molecular genetics, genomics and comparative sequence analysis.

BACKGROUND

The traditional approach to genome sequence analysis requires a primary sequence to be determined by conventional gel-based methods (typically using Applied Biosystems DNA sequencers). In this type of approach, the amount of work increases in proportion to both the length of sequence and the number of organisms tested and becomes impractical for large stretches of DNA or large numbers of organisms. For this reason, relatively few individuals within a species have been sequenced to look for polymorphic variation. Furthermore, only a few exemplary species, such as humans and E. coli, have been subject to large-scale sequencing.

Arrays of probes provide a more efficient means of analyzing variant sequences once a prototypical or reference sequence has been determined. Analysis of the hybridization pattern of probes to a target nucleic acid reveals the position, and optionally the nature, of differences between the target and reference sequence. For example, WO 95/11995 describes arrays comprising four probe sets. Comparison of the intensities of four corresponding probes from the four sets to a target sequence reveals the identity of a corresponding nucleotide in the target sequences aligned with an interrogation position of the probes. The corresponding nucleotide is the complement of the nucleotide occupying the interrogation position of the probe showing the highest intensity.

The existence of variation between a target and reference sequence can also be identified by differences in normalized hybridization intensities of probes flanking the variation when the probes are respectively hybridized to target and reference sequences. Relative loss of hybridization intensity is manifested as a "footprint" of probes flanking the point of variation between target and reference sequence (see EP 717,113, incorporated by reference in its entirety for all purposes). Additionally, hybridization intensities for multiple targets from different sources can be classified into groups or clusters suggested by the data, not defined a priori, such that isolates in a give cluster tend to be similar and isolates in different clusters tend to be dissimilar (see WO 97/29212, incorporated by reference in its entirety for all purposes).

Array-based resequencing has been used, for example, in the identification of large numbers of human polymorphisms in mitochondrial DNA and ESTs, the identification of drug-induced mutations in HIV, and analysis of mutations in p53 correlated with human cancer.

DEFINITIONS

A nucleic acid is a deoxyribonucleotide or ribonucleotide polymer in either single-or double-stranded form, including known analogs of natural nucleotides unless otherwise indicated.

An oligonucleotide is a single-stranded nucleic acid ranging in length from 2 to about 500 bases, and is typically, about 8–40, and more typically, 10–25 bases.

A probe is an oligonucleotide capable of binding to a target nucleic acid of complementary sequence through one or more types of chemical bonds, usually through complementary base pairing, usually through hydrogen bond formation. An oligonucleotide probe may include natural (i.e. A, G, C, or T) or modified bases (e.g., 7-deazaguanosine, inosine). In addition, the bases in oligonucleotide probe may be joined by a linkage other than a phosphodiester bond, so long as it does not interfere with hybridization. Thus, oligonucleotide probes may be peptide nucleic acids in which the constituent bases are joined by peptide bonds rather than phosphodiester linkages. See Nielsen et al., Science 254, 1497–1500 (1991).

Specific hybridization refers to the binding, duplexing, or hybridizing of a molecule only to a particular nucleotide sequence under stringent conditions when that sequence is present in a complex mixture (e.g., total cellular) DNA or RNA. Stringent conditions are conditions under which a probe will hybridize to its target subsequence, but to no other sequences. Stringent conditions are sequence-dependent and are different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide. For example, conditions of 5×SSPE (750 mM NaCl, 50 mM Na phosphate, 5 mM EDTA, pH 7.4) and a temperature of 25–30° C. are suitable for allele-specific probe hybridizations.

A perfectly matched probe has a segment perfectly complementary to a particular target sequence. Complementary base pairing means sequence-specific base pairing which includes e.g., Watson-Crick base pairing or other forms of base pairing such as Hoogsteen base pairing. Probes typically have a segment of complementarity of 6–20 nucleotides, and preferably, 10–25 nucleotides. Leading or trailing sequences flanking the segment of complementarity can also be present. The term "mismatch probe" refer to probes whose sequence is deliberately selected not to be perfectly complementary to a particular target sequence. Although the mismatch(es) may be located anywhere in the mismatch probe, terminal mismatches are less desirable as a terminal mismatch is less likely to prevent hybridization of the target sequence. Thus, probes are often designed to have the mismatch located at or near the center of the probe such that the mismatch is most likely to destabilize the duplex with the target sequence under the test hybridization conditions.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair.

An array including a pooled probe means that a cell in the array is occupied by pooled mixture of probes. For example, a cell might be occupied by probes ACCC<u>T</u>CCA and ACCC<u>C</u>CCA, in which case, the underline position is described as a pooled position. Although the identity of each probe in the mixture is known, the individual probes in the pool are not separately addressable. Thus, the hybridization signal from a cell is the aggregate of that of the different probes occupying the cell.

The term species variant refers to a gene sequence that is evolutionarily and functionally related between species. For example, in the human genome, the human CD4 gene is the cognate gene to the mouse CD4 gene, since the sequences and structures of these two genes indicate that they are highly homologous and both genes encode a protein which functions in signaling T-cell activation through MHC class II-restricted antigen recognition.

Percentage sequence identity is determined between optimally aligned sequences from computerized implementations of algorithms such as GAP, BESTFIT, FASTA, and TFASTA in the Wisconsin Genetics Software Package Release 7.0, Genetics Computer Group, 575 Science Dr., Madison, Wis.

SUMMARY OF THE CLAIMED INVENTION

The invention provides iterative methods of analyzing a target sequence, which represents a variant of a reference sequence. The methods employ an array of probes which includes a probe set comprising probes complementary to the reference sequence. A target nucleic acid is hybridized to the array of probes. The relative hybridization intensities of the probes to the target nucleic acid are then determined. The relative hybridization intensities are used to estimate a sequence of the target nucleic acid. A further array of probes is then provided comprising a probe set comprising probes complementary to the estimated sequence of the target nucleic acid. The target nucleic acid is then hybridized to the further array of probes and the relative hybridization of the probes to the target nucleic acid is determined. The sequence of the target nucleic acid is then reestimate from the relative hybridization intensities of the probes. The cycles of hybridization and estimating the sequence of the target nucleic acid can be reiterated, if desired, until the reestimate sequence of the target nucleic acid is the true sequence of the target nucleic acid.

The methods are particularly useful for analyzing a target nucleic acid that represents a species variant of a known reference sequence. For example, the reference sequence can be from a human and the target sequence from a primate. Typically, the target nucleic acid shows 50–99% sequence identity with the reference sequence. The methods are also particularly useful in situations where a target sequence differs from a reference sequence by more than one mutation within a probe length.

The methods can readily accommodate a reference sequence of at least 1 or 10 kb long or even a complete or substantially complete human chromosome or genome. A probe set for use in the methods typically includes overlapping probes that are perfectly complementary to and span the reference sequence, and the further array comprises probes that are perfectly complementary to and span the estimate sequence.

In some methods, the array of probes comprises four probe sets. A first probe set comprises a plurality of probes, each probe comprising a segment of at least six nucleotides exactly complementary to a subsequence of the reference sequence, the segment including at least one interrogation position complementary to a corresponding nucleotide in the reference sequence. Second, third and fourth probe sets, each comprise a corresponding probe for each probe in the first probe set, the probes in the second, third and fourth probe sets being identical to a sequence comprising the corresponding probe from the first probe set or a subsequence of at least six nucleotides thereof that includes the at least one interrogation position, except that the at least one interrogation position is occupied by a different nucleotide in each of the four corresponding probes from the four probe sets. In such methods, the target sequence can be estimated by comparing the relative specific binding of four corresponding probes from the first, second, third and fourth probe sets. A nucleotide in the target nucleic acid is then assigned as the complement of the interrogation position of the probe having the greatest specific binding. Other nucleotides in the target sequence are assigned by similar comparisons.

The invention also provides methods of analyzing a target nucleic acid comprising the following steps. An array of probes is designed to be complementary to an estimated sequence of the target nucleic acid. The array of probes is hybridized to the target nucleic acid. The target sequence is reestimated from hybridization pattern of the array to the target nucleic acid. The steps are the repeated at least once.

DETAILED DESCRIPTION

1. General

The invention provides improved methods for analyzing variants of a reference sequence using arrays of probes. The methods are particularly useful for target sequences showing substantial variation from a reference sequence, as may be the case where target sequence and reference sequence are from different species. The methods involve designing a primary array of probes based on a known reference sequence. Effectively, the reference sequence serves as a first estimate of sequence of the target nucleic acid. The primary array of probes is hybridized to a target nucleic acid, and the sequence of the target is estimated as well as possible from its hybridization pattern to the primary array. A secondary array of probes is then designed based on the estimated sequence of the target nucleic acid. The target nucleic acid is then hybridized with the secondary array of probes, and the sequence is reestimated from the resulting hybridization pattern. Further cycles of array design and estimation of target sequence can be performed in an iterative fashion, if desired, until the estimated sequence is constant between successive cycles.

2. Reference Sequences

Reference sequences for polymorphic site identification are often obtained from computer databases such as Genbank, the Stanford Genome Center, The Institute for Genome Research and the Whitehead Institute. The latter databases are available at world wide web genome.wi.mit.edu; world wide web shgc.stanford.edu and world wide web tigr.org. Reference sequences are typically from well-characterized organisms, such as human, mouse, *C. elegans*, Arabidopsis, Drosophila, yeast, *E. coli* or *Bacillus subtilis*. A reference sequence can vary in length from 5 bases to at least 1,000,000 bases. References sequences are often of the order of 100–10,000 bases. The reference sequence can be from expressed or nonexpressed regions of the genome. In some methods, in which RNA samples are used, highly expressed reference sequences are sometimes preferred to avoid the need for RNA amplification. The function of a reference sequence may or may not be known. Reference sequences can also be from episomes such as mitochondrial DNA. Of course, multiple reference sequences can be analyzed independently.

3. Target Nucleic Acid Sample Preparation

Targets can represent allelic, species, induced or other variants of reference sequences. Considerable diversity is possible between reference and target sequence. Target sequences usually show between 50–99%, 80–98%, 90–95% sequence identity. For example, a human reference sequence can be used as the starting point for analysis of primates, such as gorillas, orangutans, other mammals, reptiles, birds, plants, fungi or bacteria.

The nucleic acid samples hybridized to arrays can be genomic, RNA or cDNA. Nucleic acid samples are usually subject to amplification before application to an array. An individual genomic DNA segment from the same genomic location as a designated reference sequence can be amplified by using primers flanking the reference sequence. Multiple genomic segments corresponding to multiple reference sequences can be prepared by multiplex amplification including primer pairs flanking each reference sequence in the amplification mix. Alternatively, the entire genome can be amplified using random primers (typically hexamers) (see Barrett et al., *Nucleic Acids Research* 23, 3488–3492 (1995)) or by fragmentation and reassembly (see, e.g., Stemmer et al., *Gene* 164, 49–53 (1995)). Nucleic acids can also be amplified by cloning into vectors and propagating the vectors in a suitable organism. YACs, BACs and HACs are useful for cloning large segments of genomic DNA.

Genomic DNA can be obtained from virtually any tissue source (other than pure red blood cells). For example, convenient tissue samples include whole blood, semen, saliva, tears, urine, fecal material, sweat, buccal, skin and hair.

RNA samples are also often subject to amplification. In this case amplification is typically preceded by reverse transcription. Amplification of all expressed mRNA can be performed as described by commonly owned WO 96/14839 and WO 97/01603. In some methods, in which arrays are designed to tile highly expressed sequences, amplification of RNA is unnecessary. The choice of tissue from which the sample is obtained affects the relative and absolute levels of different RNA transcripts in the sample. For example, cytochromes P450 are expressed at high levels in the liver.

4. Methods of Amplification

The PCR method of amplification is described in *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202 (each of which is incorporated by reference for all purposes). Nucleic acids in a target sample are usually labelled in the course of amplification by inclusion of one or more labelled nucleotides in the amplification mix. Labels can also be attached to amplification products after amplification e.g., by end-labelling. The amplification product can be RNA or DNA depending on the enzyme and substrates used in the amplification reaction.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA,* 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

5. Probe Arrays

An array of probes contain at least a first set of probes that are complementary to a reference sequence (or regions of interest therein). Typically, the probes tile the reference sequence. Tiling means that the probe set contains overlapping probes which are complementary to and span a region of interest in the reference sequence. For example, a probe set might contain a ladder of probes, each of which differs from its predecessor in the omission of a 5' base and the acquisition of an additional 3' base. The probes in a probe set may or may not be the same length. The number of probes can vary widely from about 5, 10, 20, 50, 100, 1000, to 10,000 or 100,000. Typically, the arrays do not contain every possible probe sequence of a given length.

Often tiling arrays have four probe sets, as described in WO 95/11995. The first probe set comprises a plurality of probes exhibiting perfect complimentarily with a reference sequence, as described above. Each probe in the first probe set has an interrogation position that corresponds to a nucleotide in the reference sequence. That is, the interrogation position is aligned with the corresponding nucleotide in the reference sequence, when the probe and reference sequence are aligned to maximize complimentarily between the two. For each probe in the first set, there are three corresponding probes from three additional probe sets. Thus, there are four probes corresponding to each nucleotide in the reference sequence. The probes from the three additional probe sets are identical to the corresponding probe from the first probe set except at the interrogation position, which occurs in the same position in each of the four corresponding probes from the four probe sets, and is occupied by a different nucleotide in the four probe sets.

A substrate bearing the four probe sets is hybridized to a labelled target sequence, which shows substantial sequence similarity with the reference sequence, but which may differ due to e.g., species variations. The amount of label bound to probes is measured. Analysis of the pattern of label revealed the nature and position of differences between the target and reference sequence. For example, comparison of the intensities of four corresponding probes reveals the identity of a corresponding nucleotide in the target sequences aligned with the interrogation position of the probes. The corresponding nucleotide is the complement of the nucleotide occupying the interrogation position of the probe showing the highest intensity. The comparison can be performed between successive columns of four corresponding probes to determine the identity of successive nucleotides in the target sequence.

In many instances of comparing four corresponding probes, one of the four probes clearly has a significantly higher signal than the other three, and the identity of the base in the target sequence aligned with the interrogation position of the probes can be called with substantial certainty. However, in some instances, two or more probes may show similar but not identical signals. In these instances, one can simply score the position as ambiguous. Alternatively, can still call a base from the probe that has the higher signal but must recognize a significant possibility of error. In general, if the ratio of signals of two probes is less than 1.2, a base call has a significant possibility of error. Ambiguous positions are most frequently due to closely spaced multiple points of variation between target and reference sequence (i.e., within a probe length). Ambiguities can also arise due to low hybridization intensity because of base composition effects.

A secondary array of probes is constructed based on the same principles as the first array, except that the first probe set is tiled based on the newly estimated sequence rather than the original reference sequence. In general, the estimated sequence includes the best estimate of base present at positions of ambiguity as noted above. If there is equal probability of two or more bases occupying a particular position in the estimated sequence, one can arbitrarily decide to include one of the bases, provide alternate tilings corresponding to the different possible bases, or include multiple pooled bases at the position. The secondary array typically has second, third and fourth probe sets designed according to the same principles as in the primary array.

The secondary array is hybridized to the same target nucleic acid as was the primary array. Bases in the target sequence are called using the same principles as described above by comparison of probe intensities to give rise to a reestimated target sequence.

The process can be repeated through further iterations, if desired. Further iteration is desirable if the estimated sequence contains a substantial number of positions, which have been estimated with a low degree of confidence (e.g., from a comparison of probe intensities differing by a factor of less than 1.2). After sufficient iterations, the estimated sequence from one cycle should converge with that from the subsequent cycle. In some instances, positions of ambiguities may remain through many cycles. These positions may be due to effects such as heterozygosity, and should be checked by other means (e.g., conventional dideoxy sequencing or de novo sequencing by hybridization to a complete array of probes a given length).

Many variations in array design and analysis are possible, as described for example in WO 95/11995; EP 717,113; WO 97/29212. Optionally, arrays tile both strands of a reference sequence. Both strands are tiled separately using the same principles described above, and the hybridization patterns of the two tilings are analyzed separately. Typically, the hybridization patterns of the two strands indicates the same results (i.e., location and/or nature of variation between target sequence and reference sequence). Occasionally, there may be an apparent inconsistency between the hybridization patterns of the two strands due to, for example, base-composition effects on hybridization intensities. Combination of results from the two strands increases the probability of correct base calling and can decrease the number of iterations required to determine the correct base sequence of a target.

In a further variation, duplicate arrays are synthesized to allow analysis of hybridization between target sequence and probes under conditions of high and low stringency. Although high stringency is generally most useful, there are some regions of target sequence where the absolute hybridization intensity is low due to base composition effects, which yield base calls with a higher degree of confidence under conditions of low stringency. Statistical combination of base calls from conditions of high and low stringency can increase the overall probability of correct base calling.

6. Synthesis and Scanning of Probe Arrays

Arrays of probe immobilized on supports can be synthesized by various methods. A preferred methods is VLSIPS™ (see Fodor et al., U.S. Pat. No. 5,143,854; EP 476, 014, Fodor et al., 1993, *Nature* 364, 555–556; McGall et al., U.S. Ser. No. 08/445,332), which entails the use of light to direct the synthesis of oligonucleotide probes in high-density, miniaturized arrays (sometimes known as chips). Algorithms for design of masks to reduce the number of synthesis cycles are described by Hubbel et al., U.S. Pat. Nos. 5,571, 639 and 5,593,839. Arrays can also be synthesized in a combinatorial fashion by delivering monomers to cells of a support by mechanically constrained flowpaths. See Winkler et al., EP 624,059. Arrays can also be synthesized by spotting monomers reagents on to a support using an ink jet printer. See id.; Pease et al., EP 728,520.

After hybridization of control and target samples to an array containing one or more probe sets as described above and optional washing to remove unbound and nonspecifically bound probe, the hybridization intensity for the respective samples is determined for each probe in the array. For fluorescent labels, hybridization intensity can be determined by, for example, a scanning confocal microscope in photon counting mode. Appropriate scanning devices are described by e.g., Trulson et al., U.S. Pat. No. 5,578,832; Stern et al., U.S. Pat. No. 5,631,734.

7. Large-Scale Resequencing

The methods described above can be used for comparative analysis of whole genomes or substantial portions thereof. To illustrate, about 300 chips at 1 Mb/chip are required to sequence 10% of a mammalian genome (i.e., all the genes and a substantial amount of their surrounding sequence). If 40 chips are synthesized on a common waver using a single mask, then only 8 mask designs are required per iteration. If 10 iterations are required, then only 80 mask designs and a total of 3000 chips are made.

Although an entire genome can be hybridized to a chip in a single experiment, it is often more useful to hybridize pools of cloned sequence representing ~1 Mb at a time. This can be done in the following way. A minimal overlapping set of physical clones is first obtained. For example, random bacterial artificial chromosome clones are generated, and ordered by hybridization or conventional methods. If necessary, regions mapping to related positions in the genome are determined. E.g., pools of clones are hybridized to an array of mapped markers. Pools of clones are then generated for hybridization (e.g., 300 pools if the resequencing capacity is 1 Mb/chip and 300 chip designs are used to analyze 1/10th a mammalian genome).

8. Applications

Some of the benefits of resequencing related genomes are:
1) Correction of sequencing errors. These are often corrected by comparative analysis. For example, if an open reading frame in one genome is frameshifted in a second closely related genome, a sequencing error is usually the cause of the difference. Any sequence differences detected can be verified in the reference genome by simply checking the primary sequencing trace data, or by further analysis.
2) Identification of promoter sequences and genes. Functionally important elements tend to be conserved. Sometimes, functional elements that are difficult to identify by direct sequence analysis (such as small exons or regulatory sequences) are revealed by identifying relatively short segments that are tightly conserved between genomes.
3) Analysis of sequences differences between differences species allows correlation between form and function. For example, the sequence of chimpanzee and human differ by ~1% overall. Further, the present methods allow comparison of a range of primate sequences, to see which sequences have evolved the most rapidly and which are highly conserved.

It will be apparent from the above that the invention includes a general concept which can be expressed concisely as follows. The invention entails the use of iterative cycles of designing an array of probes to be complementary to an estimated sequence of a target nucleic acid, and using the hybridization pattern of the array to the target nucleic acid sequence to determine a more accurate reestimated target sequence.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A method of analyzing a target nucleic acid, comprising:
   (a) designing an array of probes based on a known reference sequence, the array comprising a probe set comprising probes complementary to and spanning the known reference sequence, the probes immobilized on at least one support;
   (b) hybridizing the target nucleic acid to the array of probes, wherein the target nucleic acid has a sequence which is a variant of the reference sequence and provided the array of probes does not contain every possible probe sequence of a given length;
   (c) determining the relative hybridization of the probes to the target nucleic acid,
   (d) estimating the sequence of the target nucleic acid from the relative hybridization of the probes;
   (e) designing a further array of probes based on the estimated sequence obtained in step (d), the further array comprising a probe set comprising probes complementary to and spanning the estimated sequence of the target nucleic acid, the probes immobilized on at least one support and provided the further probe array does not contain every possible probe sequence of a given length;
   (f) hybridizing the target nucleic acid to the further array of probes;
   (g) determining the relative hybridization of the probes of the further array to the target nucleic acid;
   (h) reestimating the sequence of the target nucleic acid from the relative hybridization of the probes of the further array.

2. The method of claim 1, further comprising repeating steps (e)–(h) as necessary until the reestimated sequence of the target nucleic acid is constant between successive cycles.

3. The method of claim 1, wherein the target nucleic acid is a species variant of the reference sequence.

4. The method of claim 1, wherein the reference sequence is from a human and the target nucleic acid is from a primate.

5. The method of claim 1, wherein the target nucleic acid shows 50–99% sequence identity with the reference sequence.

6. The method of claim 1, wherein the target nucleic acid shows 80–95% sequence identity with the reference sequence.

7. The method of claim 1, wherein the reference sequence is at least 1000 nucleotides long, the array comprises a probe set comprising overlapping probes that are perfectly complementary to and span the reference sequence, and the further array comprises probes that are perfectly complementary to and span the estimated sequence.

8. The method of claim 1, wherein an estimated sequence of the target nucleic acid includes a nucleotide whose identity is ambiguous and the probe set showing perfect complementarity to the estimated sequence includes a probe having a pooled nucleotide aligned with the position of ambiguity in the target sequence.

9. The method of claim 1, wherein the reference sequence is at least 10 kb.

10. The method of claim 1, wherein the reference sequence is at least 1000 kb.

11. The method of claim 1, wherein the reference sequence includes at least 90% of the human genome and a plurality of arrays and further arrays are designed in steps (a) and (f) respectively.

12. The method of claim 1, wherein the array of probes comprises:
   (1) a first probe set comprising a plurality of probes, each probe comprising a segment of at least six nucleotides exactly complementary to a subsequence of the reference sequence, the segment including at least one interrogation position complementary to a corresponding nucleotide in the reference sequence,
   (2) second, third and fourth probe sets, each comprising a corresponding probe for each probe in the first probe set, the probes in the second, third and fourth probe sets being identical to a sequence comprising the corresponding probe from the first probe set or a subsequence of at least six nucleotides thereof that includes the at least one interrogation position, except that the at least one interrogation position is occupied by a different nucleotide in each of the four corresponding probes from the four probe sets.

13. The method of claim 12, wherein the sequence of the target nucleic acid is estimated by:
   (a) comparing the relative specific binding of four corresponding probes from the first, second, third and fourth probe sets;
   (b) assigning a nucleotide in the sequence of the target nucleic acid as the complement of the interrogation position of the probe having the greatest specific binding;
   (c) repeating (a) and (b) until each nucleotide of interest in the sequence of the target nucleic acid has been estimated.

14. The method of claim 1, wherein the sequence of the target nucleic acid differs from the reference by at least two positions within a probe length.

15. A method of analyzing a target nucleic acid, comprising:
   (a) designing an array of probes immobilized on at least one support based on an estimated sequence of the target nucleic acid, which has a sequence which is a variant of a reference sequence, provided the array does not contain every possible probe sequence of a given length, whereby the probes of the array are complementary to and span the estimated target sequence,
   (b) hybridizing the array of probes to the target nucleic acid;
   (c) determining a reestimated sequence of the target nucleic acid from the hybridization pattern of the array to the target nucleic acid sequence to; and
   (d) repeating (a)–(c) at least once with the designing step being based on the reestimated sequence of the target nucleic acid determined in step (c) of the previous cylce.

* * * * *